United States Patent [19]

Laruelle et al.

[11] Patent Number: 5,310,757

[45] Date of Patent: May 10, 1994

[54] 3,3,5-TRIMETHYLCYCLOHEXYL 2-METHYLPROPIONATE DERIVATIVES, THEIR METHOD OF PREPARATION AND THERAPEUTIC COMPOSITIONS IN WHICH THEY ARE PRESENT

[75] Inventors: Claude Laruelle, Villeneuve-Loubet; Marcel Lepant, Vence, both of France

[73] Assignee: Panmedica, Carros, France

[21] Appl. No.: 856,071

[22] PCT Filed: Nov. 12, 1990

[86] PCT No.: PCT/FR90/00806

§ 371 Date: Jun. 16, 1992

§ 102(e) Date: Jun. 16, 1992

[87] PCT Pub. No.: WO91/07373

PCT Pub. Date: May 30, 1991

[30] Foreign Application Priority Data

Nov. 13, 1989 [FR] France ................................. 89 14832

[51] Int. Cl.$^5$ ....................... A01N 37/10; C07C 69/76
[52] U.S. Cl. ................................ 514/545; 560/52; 560/43; 560/57; 560/59; 560/61; 560/62; 514/531; 514/535
[58] Field of Search ............... 560/61, 62, 43, 52; 514/545

[56] References Cited

U.S. PATENT DOCUMENTS 3,931,302  1/1976  Allais et al. ........................ 560/52
4,153,724  5/1979  Hamazaki et al. ................... 560/52

OTHER PUBLICATIONS

Metz et al, "Hypolipemic Activity of Clofibrate-Related Compounds", Arzneim.-Forsch, 25(11), 1686-92, 1975, CA 84(13): 83991g. Abstract only.

*Primary Examiner*—José G. Dees
*Assistant Examiner*—Keith MacMillan
*Attorney, Agent, or Firm*—Dickinson, Wright, Moon, Van Dusen & Freeman

[57] ABSTRACT

Derivatives of 3,3,5-trimethylcyclohexanol methyl-2-propionate, preparation method, and therapeutical compositions containing them. Such derivatives have general formula (I).

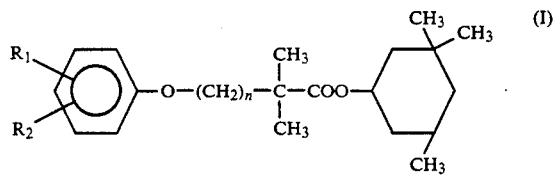

6 Claims, No Drawings

3,3,5-TRIMETHYLCYCLOHEXYL 2-METHYLPROPIONATE DERIVATIVES, THEIR METHOD OF PREPARATION AND THERAPEUTIC COMPOSITIONS IN WHICH THEY ARE PRESENT

The present invention relates to novel 3,3,5-trimethylcyclohexyl 2-methylpropionate derivatives, to their method of preparation and to the therapeutic compositions in which they are present.

Phenoxyisobutyric acids and their esters with lower alcohols have been known for a long time as hypolipidaemics and are used in therapeutics for correcting lipidaemic disorders. U.S. Pat. No. 3,907,792 describes fenofibrate, or isopropyl 4-(4-chlorobenzoyl)phenoxyisobutyrate, and is employed in therapeutics for the treatment of hypercholesterolaemia and hypertriglyceridaemia. Other analogues, such as bezafibrate, or 2-(4-(2-(4-chlorobenzamido)ethyl)phenoxy)-2-methylpropionic acid, described in U.S. Pat. No. 3,781,328, ciprofibrate, or 2-(4-(2,2-dichlorocyclopropyl)phenoxy)-2-methylpropionic acid, described in U.S. Pat. No. 3,948,973, or gemfibrozil, described in U.S. Pat. No. 3,674,836, are used as drugs and prescribed for lipidaemic disorders.

3,3,5-Trimethylcyclohexanol, on the other hand, is known for its pharmacological properties, especially vasodilating properties, and is used in cyclandelate as the mandelic acid ester. European patent application 157 151 in turn discloses 3,3,5-trimethylcyclohexyl 2-nicotinoylmandelate, which is another vasodilator. Other simple esters have been described in this same field of activity. Bisphenoxyacetic acid esters (German patent 2 326 061) and biphenyl-4-carboxylic acid esters (European patent 57 141) may be mentioned in particular.

The object of the present invention was to provide novel hypolipidaemic compounds which unexpectedly have a very much greater hypolipidaemic activity than the corresponding 2-methylpropionic acids or their esters, both on triglycerides and on cholesterol.

A further object of the invention is to provide a method of preparing said compounds.

The present invention relates to 3,3,5-trimethylcyclohexanol derivatives, characterized in that they have the general formula

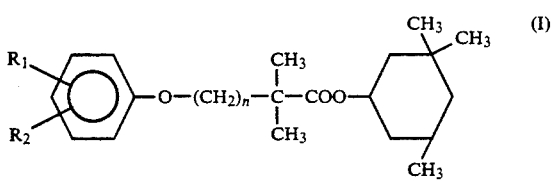

in which:

n=0, 1, 2, 3, 4 or 5 and $R_1$ and $R_2$ are identical or different and are each a hydrogen atom or one of the following substituents: —$CH_3$; —$OCH_3$; —F; —$CF_3$; ethyl; propyl; hydroxypropyl; propionyl; acetylcyclopropyl; 2,2-dichlorocyclopropyl; a 4-benzoyl group in which the benzoyl ring can be substituted by one or more of the following moieties: Cl—, F—, Br—, $CF_3$—, $CH_3$— and $CH_3O$—; a 4phenylacetyl group; a phenyl group; a 4-parachlorobenzoylaminoethyl group; or a 4-(3-phenoxypropyl) group in which the phenyl ring can be substituted by one or more moieties selected from Cl, Br, F, $CF_3$, $OCH_3$ and $CH_3$.

The preferred compounds according to the invention are:

3,3,5-trimethylcyclohexyl 2-(4-(4-chlorobenzoyl)phenoxy)-2-methylpropionate, 3,3,5-trimethylcyclohexyl 2-(4-(2,2-dichlorocyclopropyl)phenoxy)-2-methylpropionate, 3,3,5-trimethylcyclohexyl 2-(4-fluorophenoxy)-2-methylpropionate, 3,3,5-trimethylcyclohexyl 2-(3-(2,5-dimethylphenoxy)propyl)-2-methylpropionate and 3,3,5-trimethylcyclohexyl 2-(4-(2-(4-chlorobenzamido)ethyl)phenoxy)-2-methylpropionate.

In terms of the present invention, 3,3,5-trimethylcyclohexanol includes not only a mixture of its CIS and TRANS isomers but also a mixture of these isolomers enriched in either CIS or TRANS, or else each of these isomers in the pure state. Of course, each of these CIS or TRANS forms is understood as meaning each optical isomer of (R) or (S) configuration, arising from the chirality of the carbon in the 3-position to the alcohol group, or else their racemic mixture.

The compounds according to the present invention possess valuable pharmacological properties as hypolipidaemics and prove to be useful in the treatment of lipidaemic or cholesterolaemic dysfunctions both in man and in animals.

The Applicant has in fact found that the 3,3,5-trimethylcyclohexyl esters of 2-substituted 2-methylpropionic acid have very much greater antihypertriglyceridaemic, hypocholesterolaemic and hypolipidaemic activities than the corresponding 2-methylpropionic acids or their simple alkyl esters. The advantage of the products according to the present invention is that they have activities which modulate the enzymatic systems involved in cholesterol synthesis, as a consequence of which they are of particular value in the treatment of atherosclerosis.

The present invention further relates to a method of preparing the esters according to the invention, characterized in that 3,3,5-trimethylcyclohexanol is reacted with a reactive form of an appropriate carboxylic acid, of formula II below:

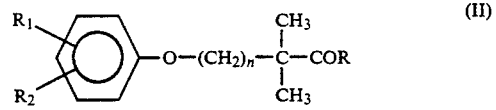

in which n, $R_1$ and $R_2$ are as defined above and R is a halogen, an alkoxy group in which the alkyl group is $C_{1-6}$, a group —O—CO—R', in which R' is a $C_{1-6}$ alkyl group or a group

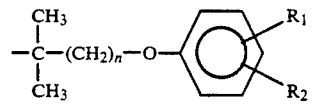

n, $R_1$ and $R_2$ being as defined above, or an OH group, in the presence of an inert solvent and, if appropriate, in the presence of a hydrogen acceptor.

When R is a halogen (especially bromine, chlorine or iodine), the reactive derivative is an acid halide; when R is an alkoxy group, the reactive derivative is an alkyl ester; when R is a group O—CO—R', the reactive derivative is an acid anhydride.

According to one advantageous mode of carrying out the method, the 3,3,5-trimethylcyclohexanol and the reactive derivative are in stoichiometric amounts.

According to another mode of carrying out the method, the 3,3,5-trimethylcyclohexanol is in excess.

According to yet another advantageous mode of carrying out the method, when R is a halogen, the reaction temperature is between 0° and the boiling point of the solvent, preferably the boiling point of the solvent.

When the 3,3,5-trimethylcyclohexanol is in excess, the excess alcohol can subsequently be removed by vacuum distillation and recovered. The reaction is carried out in a solvent which is inert towards the reactants, such as dimethylformamide or halogenoalkanes like chloroform, methylene chloride or dichloroethane. The presence of a hydrogen acceptor, although not essential, favours completion of the esterification. Mineral bases of low solubility, such as magnesia, or, preferably, tertiary amines like triethylamine or dimethylaminopyridine, may be used for this purpose.

According to another advantageous mode of carrying out the method, when R is an alkoxy group, the reaction temperature is between 60° and 110° C., said reaction being carried out in the presence of an appropriate catalyst.

The catalyst is represented for example by traces of alkali metals, their hydrides, their alcoholates or else their carbonates. Sodium or sodium hydride will preferably be used. The reaction can be carried out in a large excess of 3,3,5-trimethylcyclohexanol, which serves as the solvent medium, or with approximately stoichiometric ratios of reactants, in which case the reaction is carried out in a solvent selected from aliphatic or aromatic hydrocarbons. The chosen solvent will preferably be one which is capable of giving an azeotropic mixture with the alkanol of the starting ester; for example, octane, toluene, benzene or cyclohexane will be chosen for a methyl ester and ethyl butyl ether, heptane, hexane, toluene, benzene or cyclohexane will be chosen for an ethyl ester. After isolation of the crude products with an immiscible solvent and washing with water, the products are purified by the conventional methods, namely crystallization for the products with high melting points or absorption chromatography on silica or alumina for the oily products or products with low melting points.

According to yet another mode of carrying out the method, when R is an OH group, the reaction temperature is between 0° C. and the reflux temperature of the solvent, preferably around 0° C. at the beginning of the reaction and then room temperature thereafter, and said reaction is carried out in the presence of a coupling agent, for example N,N'-dicyclohexylcarbodiimide or N-ethyl-N'-(dimethylaminopropyl)carbodiimide, in an inert solvent.

The proportions of the reactants employed are stoichiometric and the chosen solvents are dimethylformamide or halogenated derivatives such as chloroform or methylene chloride. The dicyclohexylurea formed is filtered off and then, after a first evaporation, the residue is taken up in ethyl acetate to enable the urea to be totally removed. The product is then purified by the usual techniques already mentioned for the above experiments.

As a variant, when R is an OH group, the esterification reaction is carried out by reacting the carboxylic acid directly with trimethylcyclohexanol at a temperature slightly below the boiling point of trimethylcyclohexanol under the pressure conditions used.

This procedure is adopted especially when the chosen carboxylic acid has a good thermal stability and a sufficiently low pKa. An excess of trimethylcyclohexanol, ranging from 1 to 4 times the stoichiometric amount, is used in this case. If the operating pressure is atmospheric pressure, the reaction is carried out at between 100° C. and 190° C., preferably at around 150° C., so as to remove the water formed in the reaction by entrainment with the trimethylcyclohexanol. This temperature may be lowered if the operating pressure is reduced.

Apart from the foregoing provisions, the invention also includes other provisions which will become apparent from the following description relating to Examples of how to carry out the method forming the subject of the present invention.

It must be clearly understood, however, that these Examples are given solely in order to illustrate the subject of the invention, without in any way implying a limitation.

EXAMPLE 1: (TRANS) 3,3,5-TRIMETHYLCYCLOHEXYL 2-(4-(4-CHLOROBENZOYL)PHENOXY)-2-METHYLPROPIONATE BY REACTION OF THE ACID CHLORIDE 5 g (35 mmol) of TRANS 3,3,5-trimethylcyclohexanol and then 3.5 g (35 mmol) of triethylamine dissolved in 10 ml of chloroform are added to 50 ml of pure chloroform. The solution is stirred in the cold and 12 g (35 mmol) of 2-(4-(4-chlorobenzoyl)phenoxy)-2-methylpropionyl chloride diluted in 100 ml of chloroform are then added. The mixture is boiled for three hours and then left to stand for 24 hours. It is then washed successively with normal hydrochloric acid, then a solution of bicarbonate and finally water. After drying over anhydrous sodium sulphate, the chloroform solution is evaporated and the residue is recrystallized from ethanol to give attractive white crystals melting at 129° C., which constitute the title derivative and in TLC on a silica gel plate give a single spot of Rf 0.80 (compared with 0.40 for 3,3,5-trimethylcyclohexanol) in the solvent system petroleum ether 85%/ethyl acetate 15%. The plate can be developed by exposure to UV light of 254 nm or by spraying with a solution of vanillin in sulphuric acid (blue-violet spot for 3,3,5-trimethylcyclohexanol and its ester).

The IR spectrum (run in KBr) has the following characteristic bands: 2950 to 2850 cm$^{-1}$ for —CH$_2$— and —CH$_3$; three strong bands at 1735, 1660 and 1600 cm$^{-1}$ for the carboxylic acid esters.

EXAMPLE 2: (CIS) 3,3,5-TRIMETHYLCYCLOHEXYL 2-(4-(4-CHLOROBENZOYL)PHENOXY)-2-METHYLPROPIONATE 5 g of 3,3,5-trimethylcyclohexanol, CIS form, and then 3.5 g of triethylamine dissolved in 10 ml of chloroform are added to 50 ml of pure chloroform. 12 g of 2-(4-(4-chlorobenzoyl)phenoxy)-2-methylpropionyl chloride diluted in a few ml of chloroform are then added slowly to the solution at low temperature. The mixture is refluxed for three hours and then, after cooling, the organic layer is washed successively with a normal solution of hydrochloric acid, sodium hydroxide and then distilled water. It is evaporated under reduced pressure and the residue is then chromatographed on a silica column with a mixture of petroleum ether and ethyl acetate and finally recrystallized from ethanol to give the title derivative in the form of attractive white crystals melting at 65° C., which in thin layer chromatography give a single spot of Rf 0.45 in the solvent system described in Example 1.

The IR spectrum run in KBr has the same characteristic bands at 2950–2850, 1735, 1660 and 1600 cm$^{-1}$ as that of the previous Example, but shows significant differences between 1000 and 600 cm$^{-1}$.

EXAMPLE 3: (TRANS) 3,3,5-TRIMETHYLCYCLOHEXYL 2-(4-(2-(4-CHLOROBENZAMIDO)ETHYL)-PHENOXY)-2-METHYLPROPIONATE 12.5 g (0.034 mol) of 2-(4-(2-parachlorobenzamidoethyl)phenoxy)-2-methylpropionic acid are dissolved in 100 ml of anhydrous dimethylformamide, and 4.8 g of 3,3,5-trimethylcyclohexanol (transform) (0.034 mol) and 0.5 g of dimethylaminopyridine are added. After solubilization, a solution of 7 g of dicyclohexylcarbodiimide (0.034 mol) in 20 ml of dimethylformamide is added slowly at a temperature of around 0° C. The reaction is allowed to continue for 24 hours at ordinary temperature and the precipitate of dicyclohexylurea is filtered off; after evaporation of the filtrate under reduced pressure, the residue is chromatographed on a silica column in a mixture of petroleum ether and ethyl acetate. After evaporation of the solvent, the title derivative is obtained in the form of white crystals melting at 100° C.; the yield is 45%. This product, chromatographed under the conditions of Example 1, shows a single spot of Rf 0.2. The IR spectrum run in KBr has the following characteristic bands: one broad band at 3250 cm$^{-1}$, a group of fine bands at 3000–2840 cm$^{-1}$ an strong bands at 1750 cm$^{-1}$ and 1640 cm$^{-1}$.

EXAMPLE 4: (CIS) 3,3,5-TRIMETHYLCYCLOHEXYL 2-(4-(2-(4-CHLOROBENZAMIDO)ETHYL)-PHENOXY)-2-METHYLPROPIONATE

The reaction is carried out under the same conditions as in Example 3 and with the same proportions of reactants. After chromatography on a silica column, the product can be recrystallized from ethyl acetate to give the title derivative in the form of white crystals melting at 122° C. (capillary). Thin layer chromatography under the conditions already described shows a single spot whose Rf of 0.2 is identical to that of the product of Example 3. The IR spectrum run in KBr has the same principal characteristic bands as in Example 3, although the fine bands between 1000 and 600 cm$^{-1}$ are markedly different.

EXAMPLE 5: (CIS) 3,3,5-TRIMETHYLCYCLOHEXYL 2-(3-(2,5-DIMETHYLPHENOXY)PROPYL)-2-METHYLPROPIONATE 25 g of 2-(3-(2,5-dimethylphenoxy)propyl)-2-methylpropionyl chloride are added to 14 g of (cis) 3,3,5-trimethylcyclohexanol dissolved in 100 ml of toluene. The mixture is refluxed for three hours and then evaporated to dryness. The evaporation residue is chromatographed on a silica column with chloroform. The title product is obtained in the amorphous state and in thin layer chromatography gives a single spot under the above conditions; the characteristic bands of its IR spectrum run in KBr are as follows: 3000–2850 cm$^{-1}$, group of fine bands; 1730 cm$^{-1}$, strong band for the carbonyl.

EXAMPLE 6: (TRANS) 3,3,5-TRIMETHYLCYCLOHEXYL 2-(3-(2,5-DIMETHYLPHENOXY)PROPYL)-2-METHYLPROPIONATE

The reaction is carried out under the conditions of the above Example and with the same proportions of reactants, but this time using (TRANS) 3,3,5-trimethylcyclohexanol, to give the product according to the present Example in the amorphous state; it has the same physical and chromatographic characteristics as the product of the previous Example. The IR spectrum has the same characteristic bands as the derivative according to Example 5, differences being observed only in the 1000 to 600 cm$^{-1}$ region.

EXAMPLE 7: (TRANS) 3,3,5-TRIMETHYLCYCLOHEXYL 2-(4-PHENYLPHENOXY)-2-METHYLPROPIONATE 27 g of methyl 2-(4-phenylphenoxy)-2-methylpropionate (0.1 mol) and 0.3 g of sodium hydride as a 60% dispersion in oil are added to 14.2 g of (trans) 3,3,5-trimethylcyclohexanol (0.1 mol) dissolved in 500 ml of heptane. The stirred mixture is brought to the boil in a distillation apparatus appropriately equipped for progressively separating the binary heptane/methanol mixture, which boils at 59° C.; the operation requires 4 to 5 hours; the mixture is cooled and then washed carefully with an alkaline aqueous solution, then an acidic aqueous solution and finally pure water. After chromatography on a silica column with a mixture of ethyl acetate and petroleum ether and recrystallization from 90% isopropanol, the title derivative is obtained in the form of silky crystals melting at 96° C. TLC performed under the previous conditions gives a single spot of Rf 0.90. The IR spectrum has characteristic bands at 2950–2850, 1745 and 1640 cm$^{-1}$.

EXAMPLE 8: (CIS) 3,3,5-TRIMETHYLCYCLOHEXYL 2-(4-PHENYLPHENOXY)-2-METHYLPROPIONATE

The procedure of the previous Example is followed, this time using the cis isomer. The title derivative is obtained in the form of unctuous crystals melting at between 76° and 80° C. The IR spectrum is identical to that of the previous Example, except for the fine bands at around 1000 to 800 cm$^{-1}$.

The following derivatives are obtained by using the conditions of the previous Example with the appropriate methyl ester:

EXAMPLE 9: (TRANS) 3,3,5-TRIMETHYLCYCLOHEXYL 2-(4-PROPIONYLPHENOXY)-2-METHYLPROPIONATE

EXAMPLE 10: (CIS) 3,3,5-TRIMETHYLCYCLOHEXYL 2-(4-PROPIONYLPHENOXY)-2-METHYLPROPIONATE

EXAMPLE 11: (TRANS) 3,3,5-TRIMETHYLCYCLOHEXYL 2-(4-ACETYL-2-CHLOROPHENOXY)-2-METHYLPROPIONATE

EXAMPLE 12: (CIS) 3,3,5-TRIMETHYLCYCLOHEXYL 2-(4-ACETYL-2-CHLOROPHENOXY)-2-METHYLPROPIONATE

EXAMPLE 13: (TRANS) 3,3,5-TRIMETHYLCYCLOHEXYL 2-(3-ACETYLPHENOXY)-2-METHYLPROPIONATE

EXAMPLE 14: (CIS) 3,3,5-TRIMETHYLCYCLOHEXYL 2-(3-ACETYLPHENOXY)-2-METHYLPROPIONATE

EXAMPLE 15: (TRAMS) 3,3,5-TRIMETHYLCYCLOHEXYL 2-(4-ACETYLPHENOXY)-2-METHYLPROPIONATE

EXAMPLE 16: (CIS) 3,3,5-TRIMETHYLCYCLOHEXYL 2-(4-ACETYLPHENOXY)-2-METHYLPROPIONATE

EXAMPLE 17: (TRANS) 3,3,5-TRIMETHYLCYCLOHEXYL 2-(4-PHENYLACETYLPHENOXY)-2-METHYLPROPIONATE

EXAMPLE 18: (CIS) 3,3,5-TRIMETHYLCYCLOHEXYL 2-(4-PHENYLACETYLPHENOXY)-2-METHYLPROPIONATE

EXAMPLE 19: (TRANS) 3,3,5-TRIMETHYLCYCLOHEXYL 2-(4-PHENOXYBUTYL)-2-METHYLPROPIONATE

EXAMPLE 20: (CIS) 3,3,5-TRIMETHYLCYCLOHEXYL 2-(4-PHENOXYBUTYL)-2-METHYLPROPIONATE

EXAMPLE 21: (CIS) 3,3,5-TRIMETHYLCYCLOHEXYL 2-(4-(2,4-DIMETHYLPHENOXY)-BUTYL)-2-METHYLPROPIONATE

EXAMPLE 22: (CIS) 3,3,5-TRIMETHYLCYCLOHEXYL 2-(4-(3,5-DIMETHYLPHENOXY)-BUTYL)-2-METHYLPROPIONATE

The compounds according to the present invention were subjected to toxicity checks performed on mice weighing from 20 to 25 grams. The administration routes were oral and intraperitoneal. The $LD_{50}$ values according to the method of Miller and Taister are all above 2000 mg/kg.

The hypolipidaemic, antihypercholesterolaemic and antihypertriglyceridaemic activities and the activities inhibiting the enzymatic systems which synthesize cholesterol were found to be greater than those of the reference products. The Table below summarizes the results of the pharmacological studies carried out especially by means of the test for the hyperlipidaemia caused by TRITON 1339. The experimental protocol was that published by J. C. FRUCHARD et al. (Gaz. Med. France, 3rd inter. coll. 1982, Dijon, 18–22). The tests are performed on groups of 7 rats weighing from 280 to 290 g. The Triton test is carried out after oral administration for six days at a rate of 0.5 millimol per kilogram of body weight. The following lipid parameters are measured: total cholesterol, triglycerides, total lipids and HDL cholesterol. The results are summarized in Table I below.

TABLE I

| Batch | Total cholesterol mmol/l | Triglycerides mmol/l | Total lipids g/l | HDL cholesterol mmol/l |
|---|---|---|---|---|
| Control | 2 ± 0.15 | 1 ± 0.3 | 3.5 ± 0.4 | 0.7 ± 0.1 |
| Triton | 9 ± 3 | 10 ± 7 | 20 ± 10 | 0.8 ± 0.1 |
| Ex. 1 | 3.5 ± 1.4 | 0.8 ± 0.1 | 3.6 ± 0.5 | 1.5 ± 0.4 |
| Ex. 2 | 3.0 ± 0.4 | 0.5 ± 0.15 | 3.6 ± 0.2 | 2.1 ± 0.5 |
| Ex. 3 | 1.2 ± 0.7 | 1.2 ± 0.4 | 3.8 ± 0.5 | 1.6 ± 0.4 |
| Ex. 4 | 2.6 ± 0.3 | 2.5 ± 0.5 | 4.8 ± 0.7 | 2.2 ± 0.3 |
| Ex. 5 | 5.0 ± 0.8 | 2.0 ± 0.3 | 3.0 ± 0.4 | 1.0 ± 0.3 |
| Ex. 6 | 2.0 ± 0.2 | 1.7 ± 0.3 | 8.0 ± 3 | 0.9 ± 0.3 |
| Ex. 7 | 2.2 ± 0.4 | 1.1 ± 0.5 | 3.0 ± 0.5 | 1.5 ± 0.4 |
| Ex. 8 | 3.0 ± 0.2 | 6.0 ± 4 | 3.6 ± 0.2 | 1.1 ± 0.2 |
| Ex. 9 | 2.5 ± 0.6 | 1.6 ± 0.3 | 5.0 ± 0.2 | 2.0 ± 0.6 |
| Ex. 11 | 1.8 ± 0.4 | 1.0 ± 0.1 | 11 ± 5 | 1.0 ± 0.1 |
| Ex. 14 | 3.0 ± 0.3 | 6.0 ± 3.0 | 4.8 ± 0.6 | 2.1 ± 0.1 |
| Ex. 15 | 2.8 ± 0.2 | 1.7 ± 1.2 | 3.0 ± 0.3 | 1.7 ± 0.1 |

The biosynthesis of cholesterol in an isolated enzymatic system or in a cell culture from organs removed from experimental animals is inhibited by limiting the activity of the enzyme 3-hydroxy-3-methylglutaryl-CoA reductase. These products according to the invention prove to be active in the treatment of hypercholesterolaemia in man or animals and hence also in the treatment of atherosclerosis.

The inhibitory activity of the products according to the present invention was determined by the method of Kuroda et al. (Biochemica et Biophysica Acta, vol. 486, pp. 70–81 (1977)), which is a modification of the method of Shapiro et al. (Analytical Biochemistry, vol. 31, pp. 383–390 (1969)). The results are summarized in Table II, where $IC_{50}$ is the concentration of product in the experimental medium which is necessary to achieve a 50% inhibition of the 3-hydroxy-3-methylglutaryl-CoA reductase activity, expressed in nanomol.

TABLE II

| Compound of Example: | $IC_{50}$ |
|---|---|
| 2 | 37.2 |
| 3 | 39 |
| 4 | 25.6 |
| 5 | 30.1 |
| 7 | 42.5 |
| 10 | 37.6 |
| 12 | 21.9 |
| 13 | 35.7 |
| 16 | 45.9 |
| 18 | 32.9 |
| 20 | 40.5 |
| 22 | 30.2 |

Furthermore, chronic intraperitoneal administration to rats of the derivatives which are the most active in vitro makes it possible to measure the HMG-CoA red. activity "ex vivo".

Table III below shows the results obtained for inhibition of the HMG-COA red. activity compared with the reference product fenofibrate. The doses administered were 50 mg/kg for 6 days; six rats were used in each series; they are sacrificed without anaesthesia and the liver microsomes are isolated for the assay, which is performed according to the above-mentioned protocol.

TABLE III

| Product of: | Mevalonate formed | % inhibition |
|---|---|---|
| Example 1 | 4.44 | 74 |
| Example 2 | 7.3 | 57 |
| Example 5 | 6.71 | 60 |
| Example 6 | 6.01 | 65 |
| Example 17 | 8.66 | 50 |
| Example 19 | 5.2 | 70 |
| Example 21 | 3.8 | 78 |
| Fenofibrate | 4.16 | 75 |
| Control | 17 | 0 |

In view of these valuable pharmacological properties and the low toxicities recorded, these compounds can be used effectively in human or veterinary therapeutics for the treatment of lipidaemic disorders, which are a frequent cause of atheroma and consequently of vascular diseases. The products according to the invention can be administered by themselves or in association with a pharmaceutically acceptable emulsifier or solvent; they can also be prepared using a pharmaceutical expedient for modulating their rate of assimilation. The pharmaceutical compositions containing these products can be administered orally, parenterally, rectally or else transdermally. The percentage of active principle in the pharmaceutical compositions can vary within wide limits according to the patient, the mode of administration and the dosage frequency. The daily dosage can vary from 1 mg to 1000 mg/kg of body weight, preferably from 1 to 30 mg per kilograin of body weight.

As is apparent from the foregoing description, the invention is in no way limited to those modes of execution, embodiments and modes of application which have now been described more explicitly; on the contrary, it encompasses all the variants thereof which may occur to those skilled in the art, without deviating from the framework or the scope of the present invention.

We claim:

1. A 3,3,5-trimethylcyclohexanol derivative, characterized in that it has the general formula

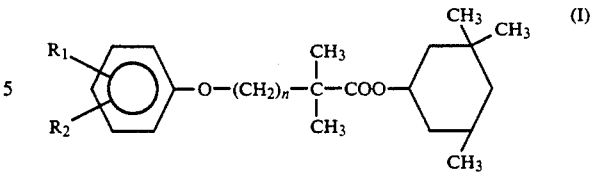

in which:

$n = 0, 1, 2, 3, 4$ or $5$ and $R_1$ is H and $R_2$ is a 4-benzoyl group in which the benzoyl ring can be substituted by one or more of the following moieties: Cl—, F—, Br—, $CF_3$—, $CH_3$—, and $CH_3O$—.

2. A derivative according to claim 1, characterized in that the 3,3,5-trimethylcyclohexanol is in one of the pure cis or trans forms or in the form of a mixture enriched to a greater or lesser extent in one of said forms.

3. A derivative according to claim 2, characterized in that the 3,3,5-trimethylcyclohexanol is in the form of one of its L or D diastereoisomers or the corresponding racemic product.

4. A derivative according to claim 1, characterized in that said derivative is CIS or TRANS 3,3,5-trimethylcyclohexyl 2-(4-(4-chlorobenzoyl)phenoxy)-2-methylpropionate.

5. A derivative according to claim 1, characterized in that said derivative is CIS or TRANS 3,3,5-trimethylcyclohexyl 2-(3-(2,5-dimethylbenzoyl)propyl)-2-methylpropionate.

6. A pharmaceutical composition containing the compound of claim 1, employed by itself or with pharmacologically acceptable adjuvants or solvents intended for oral, parenteral, rectal or transdermal administration.

* * * * *